(12) United States Patent
Thornton

(10) Patent No.: US 7,853,312 B2
(45) Date of Patent: Dec. 14, 2010

(54) SEED LOCALIZATION SYSTEM FOR USE IN AN ULTRASOUND SYSTEM AND METHOD OF USING THE SAME

(75) Inventor: Kenneth B. Thornton, Charlottesville, VA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 1525 days.

(21) Appl. No.: 10/351,453

(22) Filed: Jan. 24, 2003

(65) Prior Publication Data

US 2004/0049109 A1    Mar. 11, 2004

Related U.S. Application Data

(63) Continuation-in-part of application No. 09/875,031, filed on Jun. 7, 2001, now Pat. No. 6,549,802.

(51) Int. Cl.
*A61B 6/00* (2006.01)

(52) U.S. Cl. .................................................. 600/426

(58) Field of Classification Search ............... 600/427, 600/411, 1, 407, 424, 439, 429; 378/20, 378/62, 63, 162, 163, 164, 204, 205
See application file for complete search history.

(56) References Cited

U.S. PATENT DOCUMENTS

| | | | |
|---|---|---|---|
| 4,361,901 A | 11/1982 | Daniels et al. |
| 5,099,846 A | 3/1992 | Hardy |
| 5,447,154 A | 9/1995 | Cinquin et al. |
| 5,464,013 A | 11/1995 | Lemelson |
| 5,531,227 A | 7/1996 | Schneider |
| 5,548,627 A | 8/1996 | Swerdloff et al. |
| 5,661,773 A | 8/1997 | Swerdloff et al. |
| 5,737,506 A | 4/1998 | McKenna et al. |
| 5,751,781 A | 5/1998 | Brown et al. |

(Continued)

FOREIGN PATENT DOCUMENTS

EP    0205720 A1    12/1986

(Continued)

OTHER PUBLICATIONS

Haworth, A. et al. "Registration on Prostate Volume with Radiographically Identified Iodine-125 Seeds for Permanent Implant Evaluation" Journal of Brachytherapy International, vol. 16, No. 3, Jul.-Sep. 2000, pp. 157-167.

(Continued)

*Primary Examiner*—Brian Casler
*Assistant Examiner*—Elmer Chao
(74) *Attorney, Agent, or Firm*—Vista IP Law Group, LLP.

(57) ABSTRACT

Methods for determining a position of an implant in an ultrasound imaging system are provided. In one embodiment, the method includes determining an initial transformation matrix based at least in part on positions of a plurality of implants in a fluoroscopy coordinate system and estimated positions of said plurality of implants in an ultrasound coordinate system, modifying said initial transformation matrix based on an accuracy of said estimated positions of said plurality of implants, and determining a position of an implant in said ultrasound coordinate system based at least in part on said modified transformation. Computer program product, systems, and user interfaces associated with embodiments of the methods are also provided.

60 Claims, 10 Drawing Sheets

U.S. PATENT DOCUMENTS

| | | | |
|---|---|---|---|
| 6,006,126 | A | 12/1999 | Cosman |
| 6,049,729 | A | 4/2000 | Cook et al. |
| 6,055,295 | A | 4/2000 | Murthy et al. |
| 6,083,167 | A * | 7/2000 | Fox et al. .............. 600/439 |
| 6,122,341 | A * | 9/2000 | Butler et al. ............ 378/20 |
| 6,148,095 | A | 11/2000 | Prause et al. |
| 6,167,296 | A | 12/2000 | Shahidi |
| 6,206,832 | B1 | 3/2001 | Downey et al. |
| 6,222,544 | B1 | 4/2001 | Tarr et al. |
| 6,256,529 | B1 | 7/2001 | Holupka et al. |
| 6,311,084 | B1 | 10/2001 | Cormack et al. |
| 6,327,490 | B1 | 12/2001 | Spetz |
| 6,405,072 | B1 | 6/2002 | Cosman |
| 6,438,401 | B1 * | 8/2002 | Cheng et al. .............. 600/407 |
| 6,459,762 | B1 | 10/2002 | Wong et al. |
| 6,459,769 | B1 | 10/2002 | Cosman |
| 6,618,467 | B1 | 9/2003 | Ruchala et al. |
| 6,735,277 | B2 | 5/2004 | McNutt et al. |
| 6,799,670 | B1 * | 10/2004 | Korecki .............. 194/302 |
| 6,842,502 | B2 | 1/2005 | Jaffray et al. |
| 2002/0150207 | A1 | 10/2002 | Kapatoes et al. |
| 2003/0048868 | A1 | 3/2003 | Bailey et al. |
| 2004/0096033 | A1 | 5/2004 | Seppi |
| 2004/0114718 | A1 | 6/2004 | Brown |

OTHER PUBLICATIONS

Jaffray, D.A. et al. "A Radiographic and Tomographic Imaging System Integrated into a Medical Linear Accelerator for Localization of Bone and Soft-Tissue Targets" Int. J. Radiation Oncology Biol. Phys., 1999, vol. 45, No. 3, pp. 773-789.

International Search Report dated Jul. 27, 2005 for PCT/US03/39574.

Haworth, Annette, et al., "Registration of Prostate Volume With Radiographically Identified Iodine-125 Seeds for Permanent Implant Evaluation," 16 Journal of Brachytherapy International, No. 3, Jul.-Sep. 2000, pp. 157-167.

"Prostate Brachytherapy Made Complicated" Chapter 10: Evaluation.

* cited by examiner

SEED LOCALIZATION SYSTEM FOR USE IN AN ULTRASOUND SYSTEM AND METHOD OF USING THE SAME

RELATED APPLICATION DATA

This application is a continuation-in-part application of U.S. patent application Ser. No. 09/875,031, filed Jun. 7, 2001 now U.S. Pat. No. 6,549,802, the entirety of which is expressly incorporated by reference herein.

STATEMENT UNDER 35 U.S.C. 202(c)(6)

The U.S. Government has a paid-up license in this invention and the right in limited circumstances to require the patent owner to license others on reasonable terms as provided for by the terms of Contract No. 1 R21 CA88150-01 awarded by the Department of Health and Human Services—National Institute of Health—National Cancer Institute.

BACKGROUND AND SUMMARY OF THE INVENTION

1. Field of the Invention

This invention relates generally to systems and methods for the treatment of cancer using radiation and, more specifically, to systems and methods for the treatment of cancer using implanted brachytherapy seeds.

2. Background and Summary of the Invention

Brachytherapy, a useful technique for treating cancer, is a radiation treatment using a solid or enclosed radioisotopic source positioned on the surface of the body or a short distance from the area to be treated. With respect to the treatment of prostate cancer, for example, brachytherapy involves the implantation of radiotherapy seeds into the prostate. The effectiveness of the brachytherapy treatment depends, however, on the particularized placement of the implanted brachytherapy seeds to achieve a preferred radiotherapy dose.

The radiotherapy dose administered to the patient may be calculated by determining the three dimensional (3D) positions of the brachytherapy seeds with respect to the affected tissue. In practice, computed tomography (CT) imaging is typically used after the implant to determine both the boundaries of the affected tissue and the locations of the implanted seeds. However, most operating rooms do not have CT equipment. This makes it difficult or impossible to evaluate and subsequently adjust the dose of radiotherapy to the patient during the implant (i.e. intraoperatively). Post-operatively, if "cold spots" are found, the patient must be re-treated.

In order to intraoperatively evaluate the dosimetry to the patient imaging modalities commonly found in an operating room must be used. For many procedures, ultrasound is the preferred modality for visualizing the tissue boundaries, and fluoroscopy (X-ray) imaging is the preferred modality for visualizing the brachytherapy seeds. Despite the development of more echogenic seeds (e.g. Amersham EchoSeed™) and more sophisticated ultrasound imaging devices, it remains difficult for human observers to accurately identify implanted seeds in ultrasound data. Because seeds reflect more sound energy than tissue, they show up as relatively bright spots in the ultrasound image. Fluoroscopy images clearly show the projected 2D positions of the seeds. Because seeds absorb more X-ray energy than tissue, they show up as relatively dark spots in the fluoroscopy image. However, tissue boundaries are not clearly visualized in fluoroscopy images.

Related U.S. patent application Ser. No. 09/875,031, filed Jun. 7, 2001, discloses systems and methods for determining the positions of implanted seeds using, at least in part, markers placed inside a patient. The markers are point objects capable of being visualized in both ultrasound and fluoroscopy images. They provide the "tie points" needed to register the fluoroscopy coordinate system with the ultrasound coordinate system. In this approach, markers and tissue boundaries are visualized with ultrasound and markers and seed positions are visualized with fluoroscopy. By reconstructing 3D seed positions from the fluoroscopy images and registering them to the ultrasound images through the use of the markers, the seed positions may be localized with respect to the affected tissue boundaries and the radiotherapy dose to the patient calculated.

It is generally known that placing markers around an affected tissue provides a better geometry for registration. For example, it is known that registration is impossible if all markers lie on the same 3D line or within the same 3D plane. Various systems, such as gold seeds, needle tips, and a "dummy" probe, have been used to provide markers around affected tissue. However, as will be apparent from the following discussion, each of these systems has its disadvantages.

Gold seeds have been used as fiducial markers. Existing gold seeds, which are FDA-approved for permanent implantation, are well visualized in fluoroscopy images, but less well visualized in ultrasound images. In order to provide a geometry for better registration, the gold seeds are typically placed around an affected tissue. However, in certain situations, it may be difficult or impossible to place the gold seeds in this manner. Furthermore, gold seeds in the ultrasound images may not be easily located by either existing software or physicians. Errors in locating the gold seeds in the ultrasound images may subsequently cause an inaccurate determination of ultrasound seed positions.

Implant needle tips have been used as fiducial markers. In this technique, after inserting the seeds, the physician inserts several needles into the patient. The needle tips serve as fiducials and must be located in both the ultrasound and fluoroscopy images. Although most of the needle is well visualized in a fluoroscopy image, because the needle tip narrows to a point, the position of the tip is generally fuzzy and difficult to locate accurately. In addition, physicians may be reluctant to insert additional needles into the patient (e.g., through unused holes of a template that was previously used for inserting seeds). Furthermore, the needle tips in the ultrasound images may not be easily located by either software or physicians. Errors in locating the needle tips may subsequently cause an inaccurate determination of ultrasound seed positions.

Points on a "dummy" probe have been used as fiducial markers. In this technique, especially with regards to prostate brachytherapy applications, the physician inserts a "dummy" radio-translucent probe into the patient on which fiducial markers have been placed. The marker positions are determined by calibration, and therefore do not need to be identified in the ultrasound. The disadvantage of using this technique is that the fiducial markers are located in a nearly coplanar region and provide a very poor geometry for registration. Small errors in locating the markers in the fluoroscopy images may lead to rather large errors in the subsequently determined ultrasound seed positions.

Therefore, it would be advantageous to provide a system and/or a method that provides the capability of determining the 3D positions of brachytherapy seeds without requiring use of fiducial markers or CT imaging.

The present invention provides a system and method for determining the 3D positions of one or more implanted radiotherapy seeds with respect to an area of affected tissue, such as the prostate, so that a radiotherapy dose may be calculated. The system and method may be used to determine the 3D positions of implanted brachytherapy seeds. Alternatively, the system and method may also be used to determine 3D positions of implanted objects (or implants) other than brachytherapy seeds. The system and method use ultrasound and fluoroscopy imaging and do not require CT imaging. Furthermore, the system and method do not require the use of markers placed inside the patient.

In one aspect, the invention provides a system and a method for determining the dosimetry of an implant with increased accuracy by determining the 3D positions of one or more seeds in the most recently acquired ultrasound treatment volume, or group of ultrasound treatment data.

The present invention also provides a system and method for determining the 3D positions of one or more implanted radiotherapy seeds with respect to an area of affected tissue such that the dosimetry to the affected tissue may be determined intraoperatively, permitting dynamic adjustment of a treatment plan.

The present invention further provides a system and method for allowing visualization of a 3D geometry of an implant by providing an interactive, computer-generated, graphical user interface.

Other aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how advantages and objects of the present invention are obtained, a more particular description of the present invention briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

The present invention comprises a system and method for determining the three-dimensional (3D) positions of one or more radiotherapy seeds with respect to an area of affected tissue, such as a prostate, using ultrasound and fluoroscopy imaging, so that a radiotherapy dose may be calculated. One embodiment of the present invention may be used to determine the 3D positions of implanted brachytherapy seeds. An alternative embodiment of the invention may be used to determine the 3D positions of implanted objects other than brachytherapy seeds.

Figure 1:
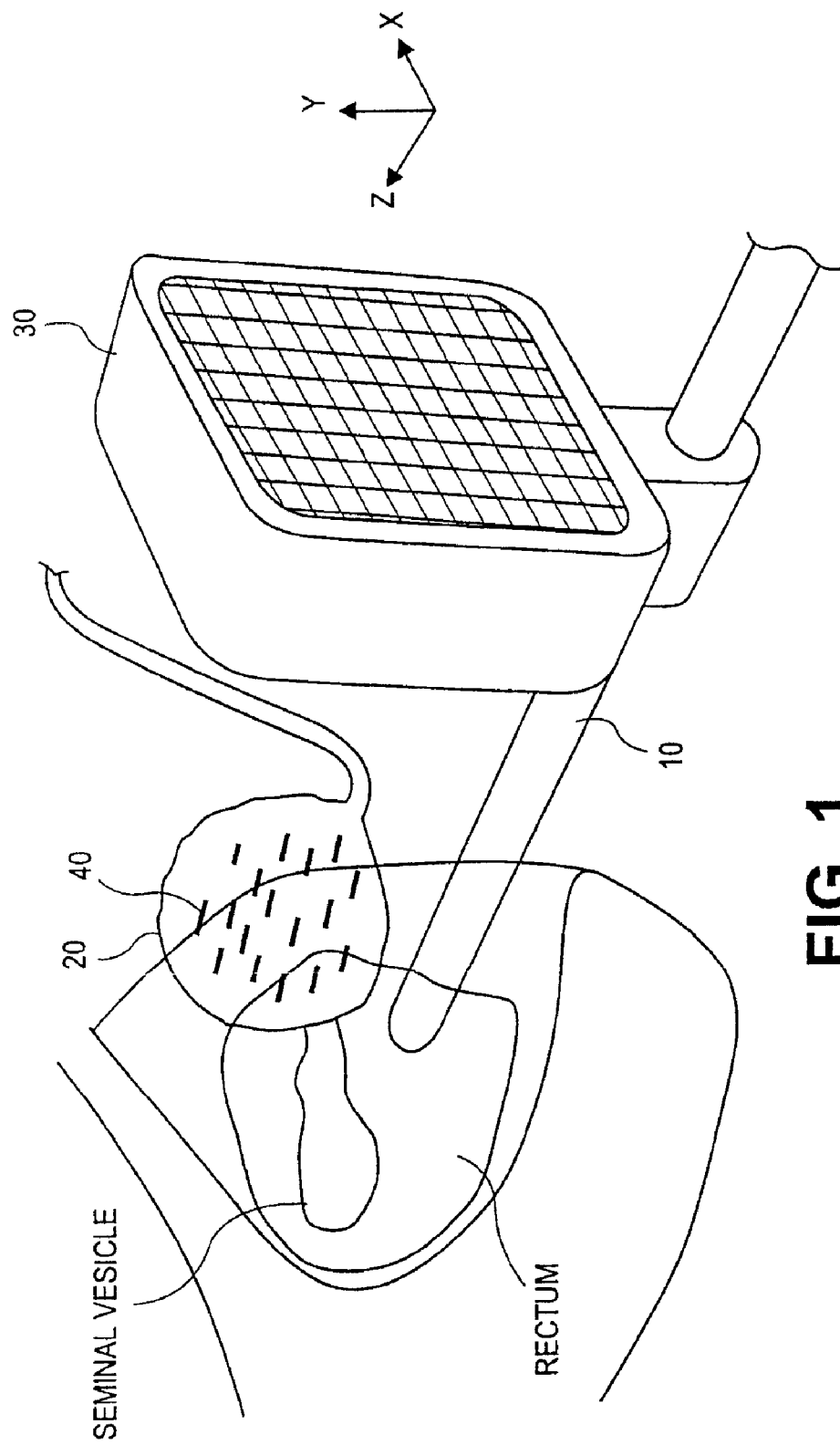
FIG. 1 is a 3D illustration of an implant geometry, particularly showing an environment in which preferred embodiments of the present invention may be operated.

Referring now to the drawings, in which similar or corresponding parts are identified with the same reference numeral, FIG. 1 illustrates a 3D view of an implant geometry and an environment in which one embodiment of the invention may be operated. As shown in FIG. 1, an ultrasound probe 10 is inserted into the rectum (beneath prostate 20) and images are formed in vertical slices through the prostate 20. These vertical image slices are planes parallel to the plane of template 30. As shown in FIG. 1, the template 30 is registered with respect to the ultrasound probe 10. Brachytherapy seeds 40 may be preloaded into hollow needles 50 (not shown) and delivered through specific pre-planned holes in the template 30. In particular, the needles 50 are inserted into the prostate 20 using the template 30 as a guide until seen on the ultrasound image appearing on an ultrasound image monitor (not shown). The therapist may then appropriately position the seeds 40 within the prostate 20. The seeds 40 are held in place by a central stylet while the needle 50 is withdrawn, leaving the seeds 40 embedded at discrete locations within a region of the prostate 20. Other methods known in the art may also be used to deliver the seeds 40 and image the prostate 20.

Typically, a therapist plans where within a region of the prostate 20 to implant the brachytherapy seeds 40. Brachytherapy seeds 40 are preferably cylinders that are 0.8 mm in diameter and 4.5 mm in length. However, implant having other geometry and/or dimension may also be used. The planned 3D position of a seed 40 is specified by a triple of (x, y, z) coordinates specifying the center of the seed 40 cylinder. The (x, y) coordinates of the triple correspond to one of the holes in the template 30. The x coordinate corresponds to a horizontal axis of the template 30, and the y coordinate corresponds to a vertical axis of the template 30. The z coordinate is the depth within the prostate 20 (i.e., some vertical plane parallel to the template 30, between the apex and the base, and orthogonal to the axes of the probe 10). Other coordinate systems may also be used.

Further details concerning radioactive seed implant planning, delivery, and verification may be found in Wallner, Kent et al., "Prostate Brachytherapy Made Complicated ($2^{nd}$ Edition)," SmartMedicine Press, Seattle, Wash., 2001, the entire disclosure of which is hereby expressly incorporated by reference into this specification as if set forth herein. Further details concerning standards for practice with respect to prostate seed implant brachytherapy may be found in articles by Nag, Subir et.al."Intraoperative Planning and Evaluation of Permanent Prostate Brachytherapy: Report of the American Brachytherapy Society," Int. J. Radiation Oncology Biol. Phys., Vol. 51, No. 5, pp. 1422-1430, 2001; Yu, Yan et al., "Permanent Prostate Seed Implant Brachytherapy: Report of the American Association of Physicists in Medicine Task Group No. 64," Medical Physics, Volume 26, No. 10, October 1999, pp. 2054-2076, and Nag, Subir et al., "American Brachytherapy Society (ABS) Recommendations for Transperineal Permanent Brachytherapy of Prostate Cancer," International Journal of Radiation Oncology Biology Physics," Volume 44, No. 4, 1999, pp. 789-799, the entire disclosures of which are hereby expressly incorporated by reference into this specification as if set forth herein.

Figure 2:
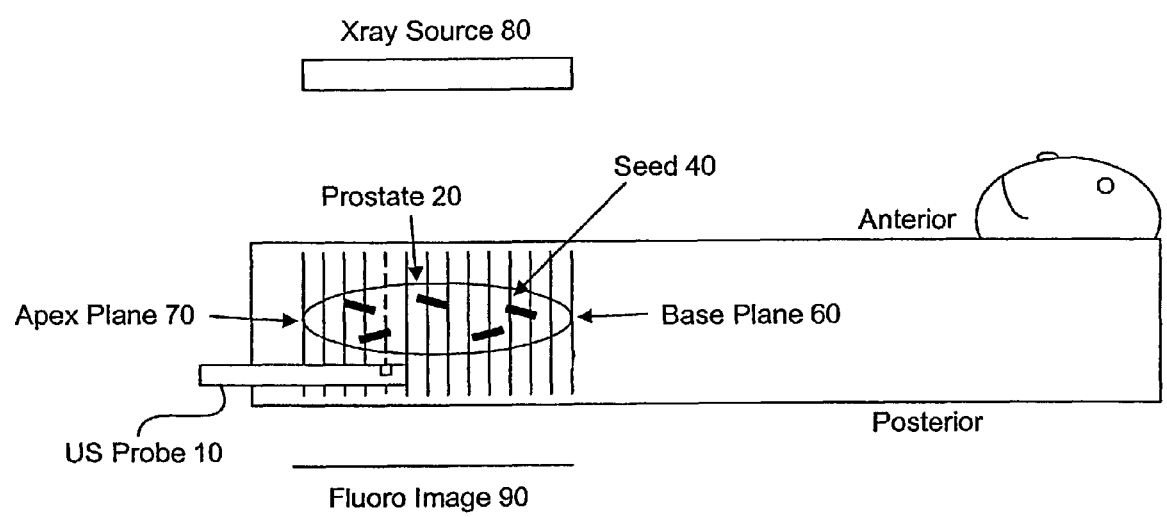
FIG. 2 is a side view of an implant geometry used with an embodiment of the present invention.

As shown in FIG. 2, seeds 40 are located in the prostate 20 at points usually between the base plane 60 and the apex plane 70. Although only five brachytherapy seeds 40 are shown, in one embodiment, 70-120 seeds may be implanted. As will be described in further detail, operation of the system or method of the present invention involves the use of imaging systems, such as, an ultrasound and fluoroscope imaging systems. FIG. 2 shows the ultrasound probe 10 of FIG. 1 for generating an ultrasound image, and an X-ray source 80 and a fluoroscopy image detector 90 for generating a fluoroscopy image. The seeds 40 are generally well visualized in fluoroscopy images, but may not always be seen in the ultrasound images.

Figure 2A:
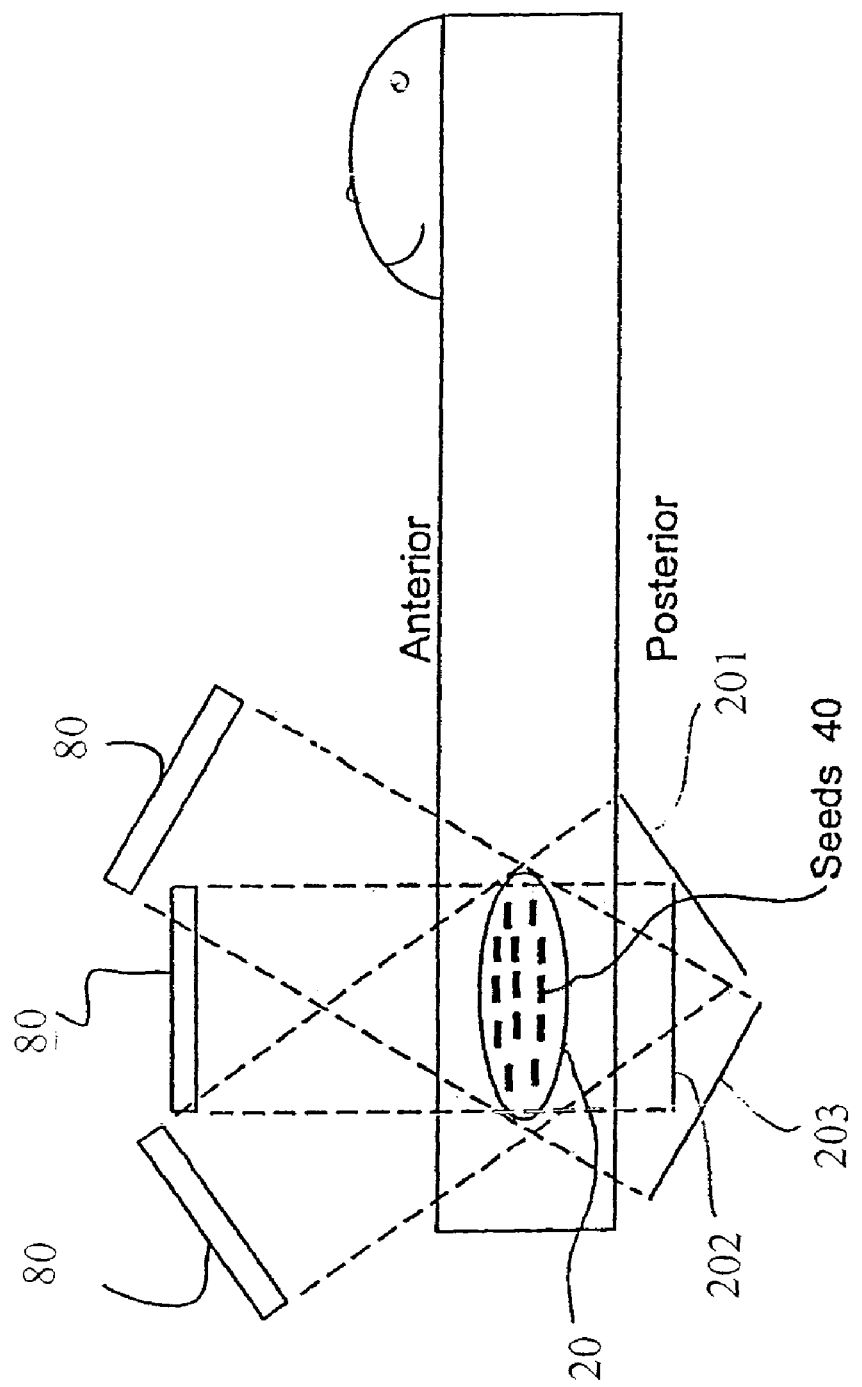
FIG. 2a is a side view illustrating fluoroscopy images being obtained at different angles.
Figure 2B:
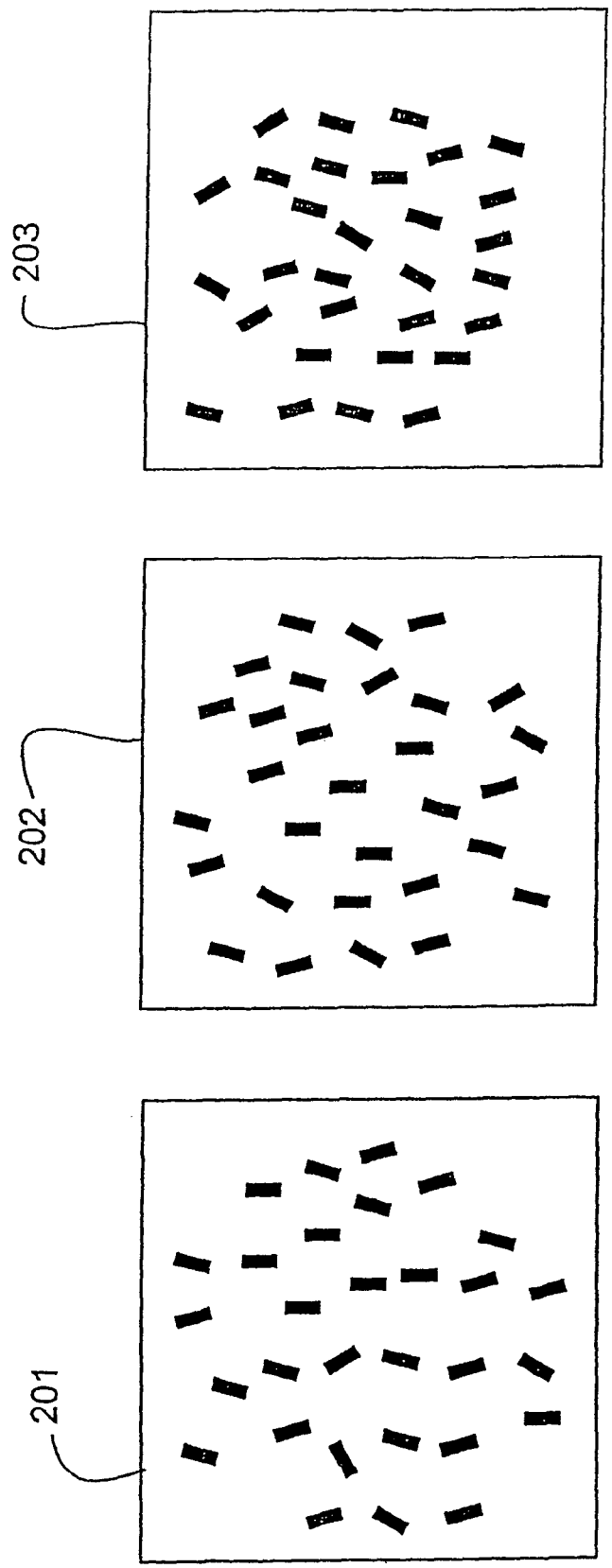
FIG. 2b is a schematic illustration of three fluoroscopy images showing the seeds.

In one embodiment, the X-ray source 80 is capable of being positioned such that several fluoroscopy images may be taken at different positions. By way of example, three fluoroscopy images 201, 202, and 203 obtained at different positions are shown in FIG. 2a. Although three fluoroscopy images are shown, the system and method described herein may obtain two or more fluoroscopy images of the seeds 40. The relative positions between the fluoroscopy images need not be predetermined. In a preferred embodiment, a user may orient the fluoroscopy imaging equipment "on-line" to maximize the visibility of seeds 40. For example, in some imaging positions, many of the seeds 40 may overlap and not be distinguishable. These positions are to be avoided. As those skilled in the art will appreciate, imaging positions with greater "disparity" (i.e., greater separation between the images) lead to more accurate 3D reconstruction of the seed positions. FIG. 2b is a schematic illustration of the three fluoroscopy images 201-203.

Figure 3:
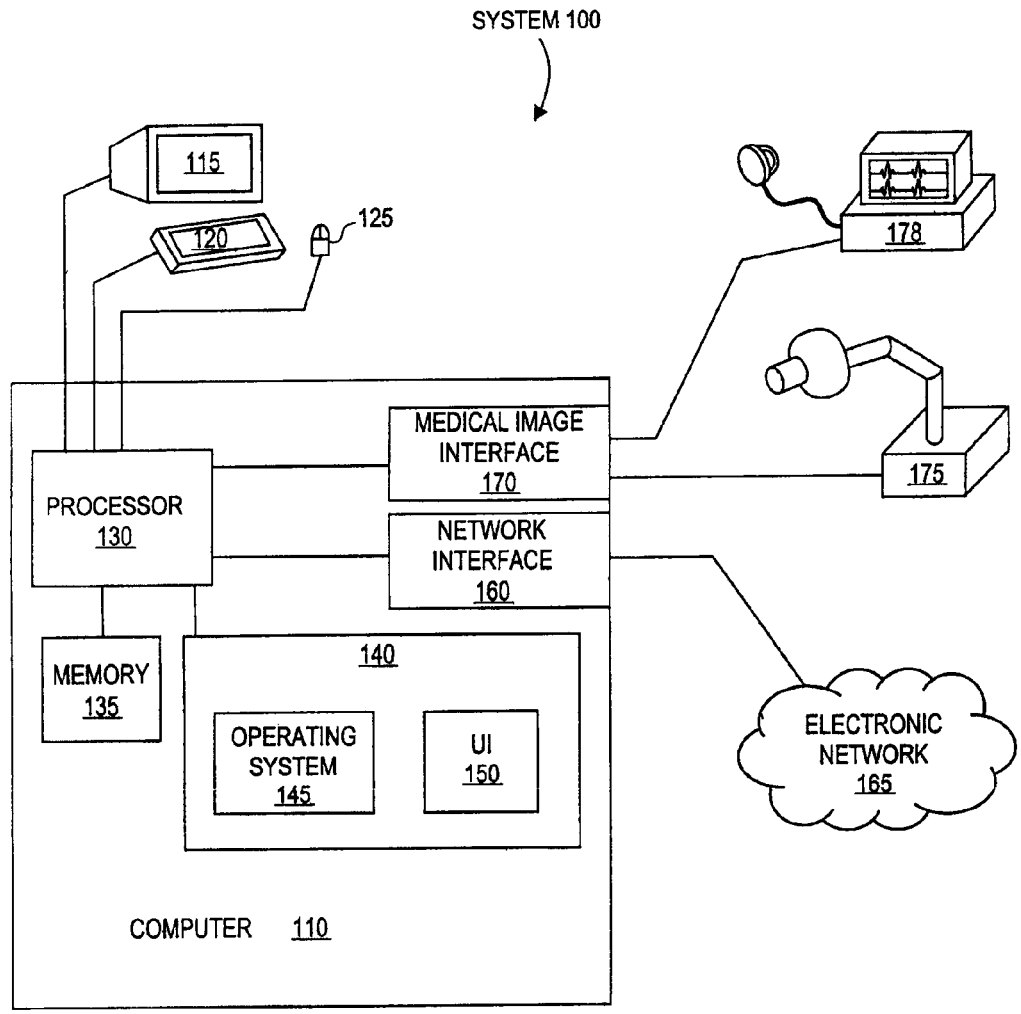
FIG. 3 is a block diagram of an embodiment of the system of the present invention.

FIG. 3 illustrates a seed localization system 100 according to an embodiment of the present invention. In one embodiment, the seed localization system 100 is implemented using programmed instructions adapted to be executed on a standard personal computer platform. In this embodiment seed localization system 100 includes a computer 110 having a standard set of peripherals, including a monitor 115, a keyboard 120, and a mouse 125. The computer 110 also includes a microprocessor 130, a memory 135, and a computer-readable medium 140. The computer-readable medium 140 may be, for example, a hard disk drive, a floppy disk drive, a CD, a floppy disk, or a server. A standard operating system software 145, such as Microsoft® Windows™, may be stored in the computer-readable medium 140. In one embodiment, the seed localization system 100 may also include a user interface 150 or other software, the execution of which allows a user to interact with the seed localization system 100. The user interface 150 may also be stored in the computer-readable medium 140.

The computer-readable media 135 or 140 may be embodied with a set of programmed instructions that cause one or more processors 130 to perform a series of steps (such as any combination of Steps 400-418, which will be discussed with reference to FIG. 4). For example, application software instructions may be implemented in the seed localization system 100 using the C or C++ programming languages. Alternatively, the system 100 may be connected to an electronic network 165 through a network interface 160 for receiving programmed instructions.

The seed localization system 100 may further include a medical image interface 170 capable of receiving signals or data from a fluoroscopy imaging device 175, and/or other imaging devices 178. The seed localization system 100 may also include one or more imaging devices, such as the ultrasound probe 10 of FIG. 1 and the fluoroscopy imaging device 175. In an alternative embodiment of the invention, the network interface 160 may be used to receive image signals or data. For example, the medical images may be obtained through the network interface 160 via a connection to the electronic network 165. The seed localization system 100 is capable of storing image data and processing stored image data in the manner described herein.

Figure 4:
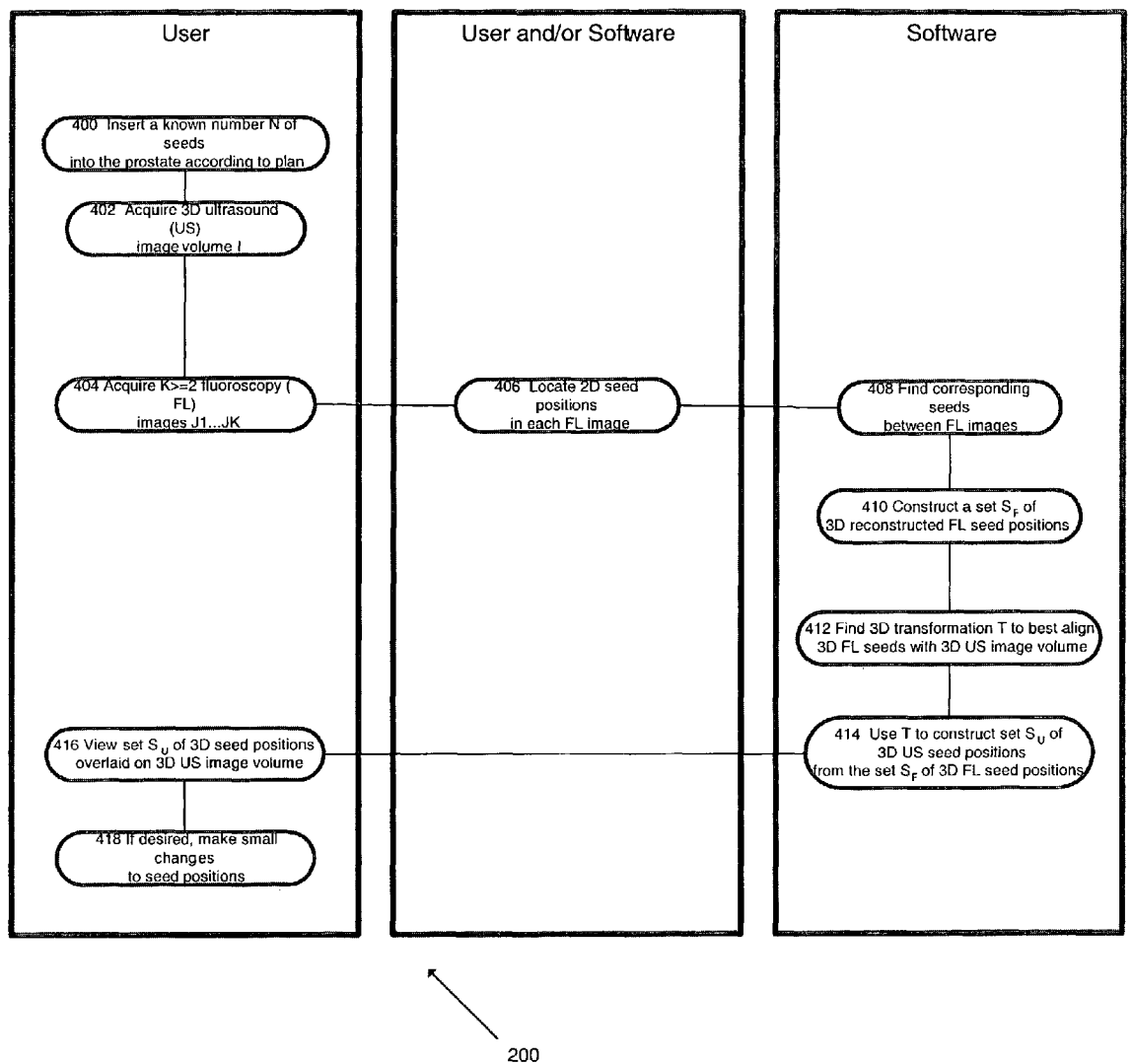
FIG. 4 is a flow chart diagram of an embodiment of a method according to the present invention.

FIG. 4 illustrates a method 200 in accordance with a preferred embodiment of the present invention. The ordering or combination of the steps may differ from that shown in FIG. 4, as would occur to one of ordinary skill in the art. Furthermore, the columns are labeled to identify the entities that perform the steps of the method in one embodiment of the invention. For example, the column labeled "User and/or Software" denotes that the steps therein may be performed by the user using the system 100, and/or automatically by the system 100, in different embodiments as described below. The column labeled "Software" denotes that the steps therein are preferably performed by the system 100, but may also be performed by the user using the system 100. It is noted that this labeling of entities is merely illustrative, and that other entities or combination of entities can be employed to practice the method described herein. As used in this specification, "ultrasound coordinate system" refers to the coordinate system used to identify the position of images in an ultrasound image space, and "fluoroscopy coordinate system" refers to the coordinate system used to identify the positions of images in a fluoroscopy image space.

First, preferably under ultrasound guidance, a physician or an operator inserts a number (N) of brachytherapy seeds 40 into a patient according to a prescribed procedure. (Step 400) Seeds 40 used in brachytherapy are preferably cylindrical with a diameter of 0.8 mm and a length of 4.5 mm, as discussed previously. However, seeds 40 having other dimensions or shapes may also be used.

Next (Step 402), a 3D ultrasound image volume I is acquired where the scalar intensity at a 3D position P in the 3D ultrasound image volume I is I(P). In one embodiment, ultrasound images have 8-bits of resolution so that if P corresponds to a point that is totally black, then I(P)=0, and if P corresponds to a point that is totally white, then I(P)=255. The 3D ultrasound image volume I represents an image volume that may be composed of equally-sized rectangular voxels. The dimensions of the voxels are preferably less than the dimensions of the implanted seeds. In one embodiment, voxel dimensions for seed imaging are 0.2 mm in the x and y dimensions and 0.5 to 1.0 mm in the z dimension. The voxel may also have other geometries and/or dimensions. The 3D ultrasound image volume may be generated by using an ultrasound imaging device, such as the probe 10, to acquire a number of 2D ultrasound images while moving the ultrasound imaging device incrementally in the direction substantially perpendicular to the planes of the 2D ultrasound images. Commercial brachytherapy treatment planning software systems, such as the VariSeed™ system from Varian Medical Systems, may also be used to acquire 3D ultrasound image volumes.

In Step 404, the user acquires $K \geq 2$ 2D fluoroscopy images $J_1, \ldots, J_k$ of the prostate 20, where the scalar intensity at 2D point p in a fluoroscopy image k is $J_k(P)$ In one embodiment, fluoroscopy images have 8-bits of resolution so that if, image k, p corresponds to a point that is totally black, then $J_k(p)=0$, and if p corresponds to a point that is totally white, then $J_k(p)=255$. Preferably, these images are "captured" directly from a fluoroscopy imaging device 175, and data associated with these images are then transmitted to the system 100 through the medical image interface 170 (as discussed with reference to FIG. 3). In another embodiment, the 2D images are loaded from a non-volatile storage 140 or received via an electronic network 190 according to standard protocols for medical images, such as "Digital Imaging and Communications in Medicine" (DICOM) protocols.

Any one of several methods or combinations thereof may be used to directly "capture" a 2D fluoroscopy image of the prostate 20. In one embodiment, a C-arm device having a x-ray source 80 and fluoroscopy image detector 90 is used. The C-arm is positioned at discrete positions that cut across the prostate 20 and such that the seeds 40 are visible in the fluoroscopy image. The acquired fluoroscopy image is then transmitted to the system 100 through the medical image interface 170. The C-arm positions at which the images are acquired do not need to be pre-determined and are chosen to maximize the visibility of the seeds 40 and to provide "maximum disparity" for image reconstruction according to standard techniques known to those skilled in the art. While fluoroscopy images are being acquired, the ultrasound probe 10 may be located within the patient, or alternatively, be placed outside the patient's body for enhanced image clarity.

In a preferred embodiment, in order in increase redundancy, three (K=3) fluoroscopy images are obtained. However, in alternative embodiments, two or more than three fluoroscopy images may be used. For the purpose of the following discussion, it will be assumed that three (K=3) fluoroscopy images are obtained in step 404.

After three (K=3) fluoroscopy images are acquired, the seeds 40 in each of the 2D fluoroscopy images may be located using the seed localization system 100. (Step 406) The seeds 40 may be well visualized in the fluoroscopy images. Because the seeds 40 may absorb more x-ray energy than tissue, the seeds 40 appear in the 2D fluoroscopy image with lesser scalar intensity, i.e., the seeds 40 show up as dark spots in the 2D fluoroscopy image. In a preferred embodiment, the seed localization system 100 automatically locates the seeds 40 using a variety of discrimination techniques known to those skilled in the art of medical imaging. Alternatively, the user of the seed localization system 100 may manually locate the seeds 40 in the 2D fluoroscopy images.

Based on the previous assumption that the system 100 acquired three (K=3) fluoroscopy images in step 404, the result of step (406) is three (K=3) sets of detected 2D points, one set per image. There may not be exactly N points in each set, because of false-alarms (points in the set that are in reality not seed positions) and misdetections (points missing from the set that should be in the set). For the purpose of the following discussion, let $\{p_{1,1},\ldots p_{1,N_1}\}$ be a set of $N_1$ points detected in the $1^{st}$ fluoroscopy image; $\{p_{2,1},\ldots,p_{2,N_2}\}$ be a set of $N_2$ points detected in the $2^{nd}$ fluoroscopy image, and $\{p_{3,1},\ldots,p_{3,N_3}\}$ be a set of $N_3$ points detected in the $3^{rd}$ fluoroscopy image.

In Step 408, the seed localization system 100 automatically matches or correlates the seed points between or among the 2D fluoroscopy images, i.e., reorders the points so that a point in one of the (K=3) fluoroscopy images corresponds with at least a point in another of the fluoroscopy images, for all N number of the seeds 40. Matching techniques known to those skilled in the art, such as the RANSAC technique, may be used. The RANSAC technique is described in *Multiple View Geometry* (Cambridge University Press, 2000), by Hartley, R. and Zisserman, A., the entirety of which is incorporated by reference herein. Other methods known in the art may also be used to correspond seeds between the fluoroscopy images.

Continuing with the previous assumption that K=3 fluoroscopy images were obtained in step 404, in step 410, the system 100 determines a set $SF=\{P_1,\ldots,P_N\}$ of 3D positions of the seeds 40 (in the fluoroscopy coordinate system) based on the geometry or position of the imaging device used to obtain the fluoroscopy images in step 404. That is, given $\{p_{k,n}|k=1,\ldots,3;n=1,\ldots,N\}$, the system estimates K=3 3×4 matrices $\{M_1,\ldots,M_K\}$ that are associated with the geometry of the imaging device (the camera matrices), and the set of reconstructed fluoroscopy 3D positions $S_F=\{P_1,\ldots,P_N\}$ to minimize the error e, where:

$$e = \sum_{k=1}^{3}\sum_{n=1}^{N}\left\|\binom{p_{k,n}}{1} - M_k\binom{P_n}{1}\right\|^2.$$

The determination of the camera matrices $\{M_1,\ldots,M_K\}$ is known in the art, and therefore, will not be discussed in further details. A closed form solution for this optimization problem is known in the literature (e.g. the Hartley and Zisserman reference given above). Because of errors in localizing the 2D positions $\{p_{k,n}|k=1,\ldots,3;n=1,\ldots,N\}$ of the fluoroscopy seeds, there will be errors in determining the 3D positions $S_F=\{P_1,\ldots,P_N\}$ of the reconstructed fluoroscopy seeds. Assuming that the 2D errors are independent and identically distributed from a 2D Gaussian distribution with zero-mean, the errors of each 3D position $P_n$ may be determined from a 3D Gaussian distribution with zero-mean and covariance matrix $\Sigma_n$. The set of covariance matrices $S_\Sigma=\{\Sigma_1,\ldots,\Sigma_N\}$ is dependent on the measured point positions $\{P_{k,n}|k=1,\ldots,3;n=1,\ldots,N\}$ and may be determined using techniques known to those skilled in the art of statistical estimation. For example, see Koch, Karl-Rudolph, *Parameter Estimation and Hypothesis Testing in Linear Models*, Springer-Verlag, 1988, the entirety of which is hereby incorporated by reference.

Figure 5:
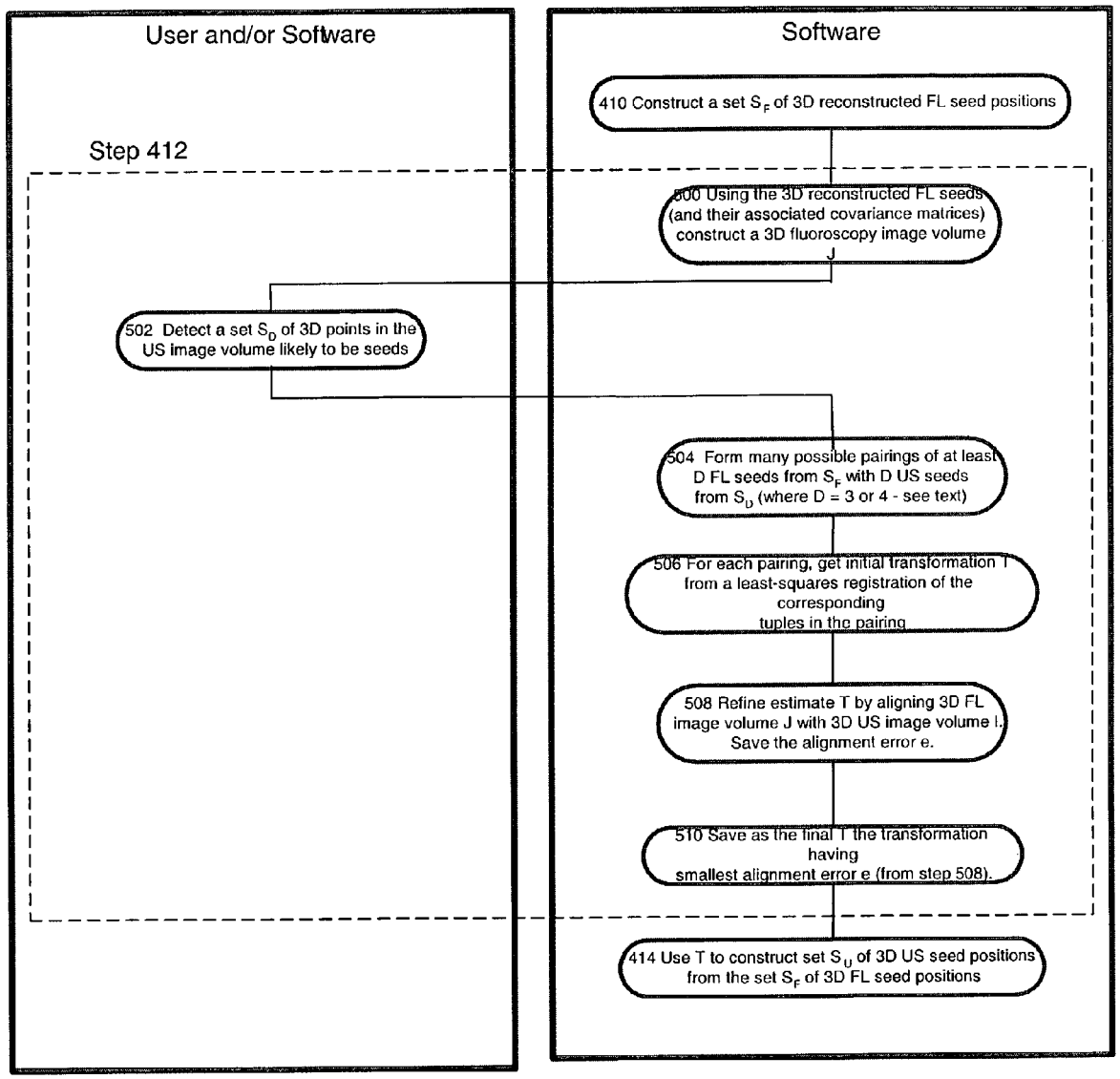
FIG. 5 is a flow chart diagram for one of the steps of FIG. 4.

In Step 412, the seed localization system 100 determines a 3D transformation T that best aligns the set of 3D coordinates $S_F=\{P_n|n=1,\ldots,N\}$ of the seeds 40 in the fluoroscopy coordinate system with the 3D ultrasound image volume I (determined from Step 402). Refer to FIG. 5, which shows that the Step 412 may include a number of sub-steps 500-510 according to a preferred embodiment of the present invention. The ordering or combination of the steps may differ from that shown in FIG. 5 as would occur to one of ordinary skill in the art.

In Step 500, using any of the known techniques, a 3D fluoroscopy image J is constructed based on the set of 3D reconstructed seed positions $S_F=\{P_n|n=1,\ldots,N\}$ and their associated 3×3 covariance matrices $S_\Sigma=\{\Sigma_n|n=1,\ldots,N\}$ determined in step (410). Each covariance matrix reflects an amount of uncertainty in the reconstructed position. For example, if $P_n$ is very certain (i.e., the reconstructed position is likely to be a location near a seed), then the scalar function $$\exp\left[-\frac{1}{2}(P-P_n)^t\sum_n^{-1}(P-P_n)\right]$$

will diminish rapidly in value as P is further away from $P_n$ (i.e., the elements of $\Sigma_n$ will be small). The opposite is true if $P_n$ is less certain. In one embodiment, the 3D fluoroscopy image J has a domain that contains, at a minimum, all of the reconstructed 3D points $\{P_n|n=1,\ldots,N\}$, and J(P) represents a characteristic, such as a color or brightness, of a voxel or pixel at location P in the fluoroscopy coordinate system. If P is unlikely to be a location near a seed (e.g., P is some arbitrary point within this domain), then J(P) will be≈0, and if P is likely to be a location near a seed, J(P) will be≈255.

In Step 502, a set of D detected points $S_D=\{\hat{P}_d|d=1,\ldots,D\}$ likely to be locations of the seeds 40 in the ultrasound coordinate system are identified. In a preferred embodiment, the identifying of the points in the ultrasound coordinate system is performed automatically by software executed by the seed localization system 100. For example, the software may implement a known discrimination technique, such as watershed segmentation (e.g., see Russ, John C., *The Image Processing Handbook* (4th Edition), CRC Press, 2002), for identifying the points. In an alternate embodiment, the user may manually identify the points that are likely to be locations of the seeds 40 in the ultrasound coordinate system. For example, the user may examine an ultrasound image of a tissue in which the seeds 40 are placed, and determines likely locations of some of the seeds 40.

Although not all of the seeds 40 may show up in the ultrasound image, not all of the seeds need to be identified. In one embodiment, the system 100 or the user identifies at least D=4 points in the ultrasound image that are likely to be locations of four of the seeds 40. As will be described below, in certain situations, and in an alternative embodiment, the system 100 or the user identifies at least D=3 points in the ultrasound image.

In step 504, points in the ultrasound coordinate system are selected and paired with coordinates of corresponding seeds 40 in the fluoroscopy coordinate system. The number of pairings selected in a group or combination may vary. If the relative position between the fluoroscopy images generated in Step 404 is known, then at least three selected points from the ultrasound system would be matched with the 3D coordinates of three corresponding seeds in the fluoroscopy coordinate system. On the other hand, if the relative position of the fluoroscopy images is not known from Step 404, then at least four selected points from the ultrasound system would be matched with the 3D coordinates of four corresponding seeds in the fluoroscopy coordinate system. The extra selected point is used in the later case because a fourth point provides a reference point for spatial definition, as will be understood by those skilled in the art. In step 504, at least one group or combination of pairings are determined.

Next, based on pairing of selected points in the ultrasound coordinate system with coordinates of corresponding seeds in the fluoroscopy coordinate system, an initial transformation $T=\{A,b\}$ for each group or combination of pairings is obtained (Step 506) by minimizing an error $$e = \sum_{(d,n)} \|\hat{P}_d - (AP_n + b)\|^2,$$

where $(\hat{P}_d, P_n)$ is one of the pairings of a detected ultrasound point with a reconstructed fluoroscopy point. A and b are components of the initial transformation T, and may be determined by methods known in the art for solving linear least-squares systems, such as the method of solution by the use of singular value decomposition (see Press, William H. et.al., *Numerical Recipes in C* (2nd Edition), Cambridge University Press, 1992). Other techniques known in the art may also be used to obtain the initial transformation T. In one embodiment, at least three pairings are used to obtain the initial transformation T. In another embodiment, at least four pairings are used to obtain the initial transformation T.

In step (508), for each combination of the pairings, the initial transformation $T=\{A,b\}$ from step (506) is refined. In one embodiment, the initial transformation T may be refined based on an accuracy (e.g., as represented by an error value) of how well the 3D ultrasound image volume I aligns with the transformed 3D fluoroscopy image J. For example, to refine $T=\{A,b\}$, an error, such as $$e = \sum_P \|I(P) - J(AP+b)\|^2,$$

may be minimized. Since this error is nonlinear in T, optimization techniques such as gradient-descent or Levenberg-Marquardt may be used. Strategies such as course-to-fine subsampling of the image volumes may also be used to make the optimization more efficient. For example, see "A Pyramid Approach to Subpixel Registration Based on Intensity," IEEE Transactions on Image Processing, Vol. 7, No. 1, January 1998, pp. 27-41, by Thevenaz, Philippe et.al., the entirety of which is hereby incorporated by reference.

In Step 510, a refined transformation T is determined and stored for later use. In one embodiment, combinations of pairings in step 504 are randomly or selectively chosen, and the error e for each combination of pairings is determined until an error e below a desired threshold value is determined. The transformation associated with the error e that is below the threshold value is then stored as the refined transformation T. Alternatively, all possible combinations of pairings are determined in step 504, and errors e for all combinations of pairings are determined. The transformation associated with the smallest error e is then stored as the refined transformation T. The refined transformation T may be stored in a medium, such as the memory 135 or the computer-readable medium 140 of the seed localization system 100, for future retrieval or processing.

Returning to FIG. 4, based on the transformation $T=\{A,b\}$ obtained from the Step 412, the seed localization system 100 determines, from the set of 3D fluoroscopy seed positions $S_F$, a set $S_U$ of 3D ultrasound seed positions, where $S_U=\{P_n'AP_n+b|n=1,\ldots,N\}$. (Step 414) The determination or calculation is preferably performed using a processor, such as the processor 130 of the seed localization system 100. However, other devices, such as a calculator, may also be used.

With the calculated 3D seed positions in the ultrasound coordinate system, identifiers associated with the calculated 3D seed positions may be displayed in the 3D ultrasound image. (Step 416) For example, cylindrical seeds 40 may be displayed as transparent cylinders having colored outline, and be shown with a 3D ultrasound image displayed on the monitor 115 of the seed localization system 100. In this manner, the user may examine the calculated positions of the seeds 40 with respect to the ultrasound image by viewing the image displayed on the monitor 115. The identifiers associated with the calculated 3D seed positions may be presented to the user via a graphical user interface (GUI). An example of such GUI is shown in FIG. 7, which will be described in further detail below.

If it is desired, the operator may optionally make small changes to the calculated positions of the seeds 40. (Step 418) For example, a user interface may be provided that allows the user to modify a calculated seed position. In one embodiment, the user interface may include a field displayed in a screen. The operator may manually type in a position for a particular seed 40 in the field to over-ride the calculated position. Alternatively, the user interface may include a button, which allows the operator to adjust the calculated position of a seed 40. Furthermore, the user interface may also include a pointer, which the operator may use to select and/or drag an identifier of a seed 40 displayed in the monitor 115.

Figure 6:
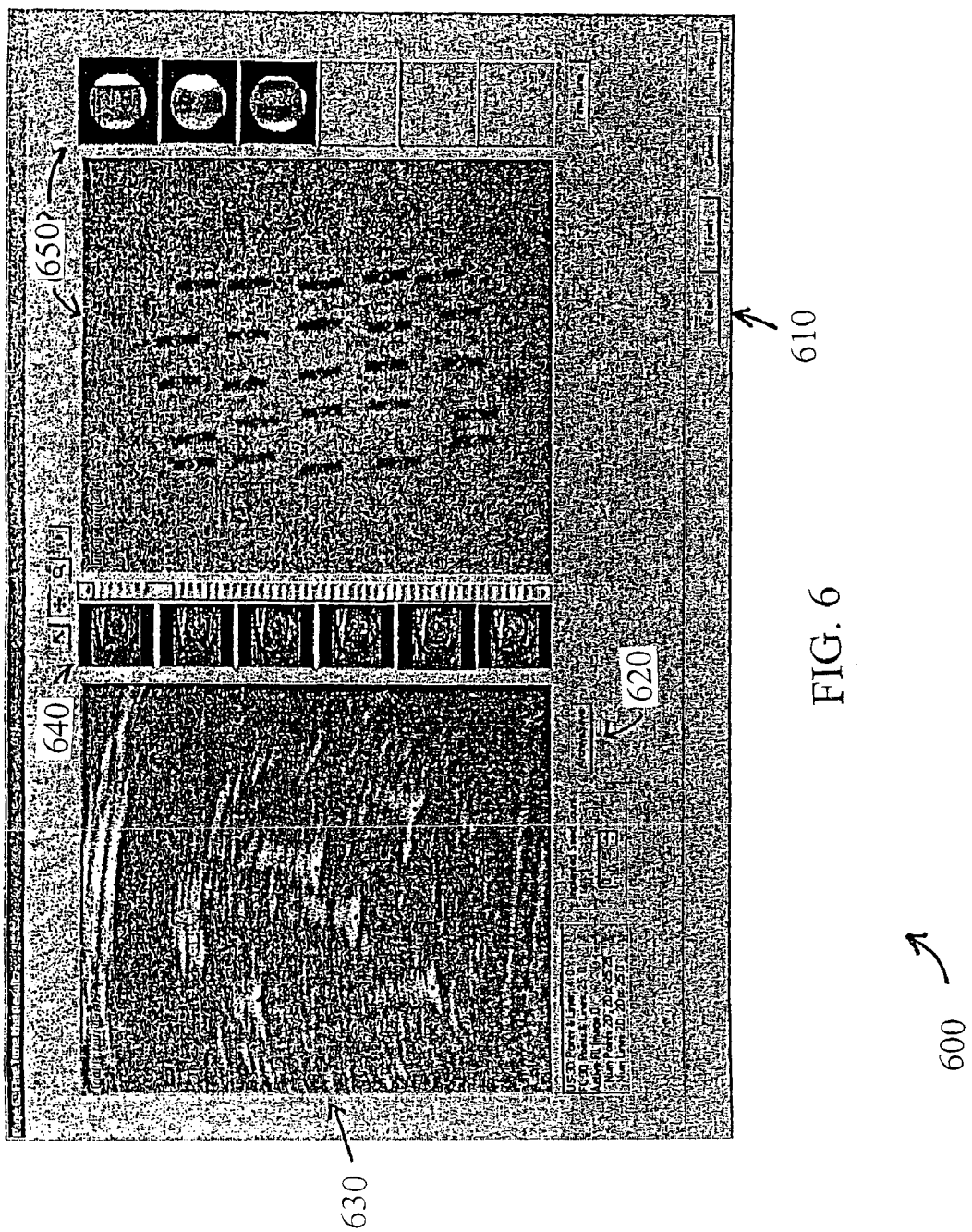
FIG. 6 is a screen shot display of a graphical user interface according to one embodiment of the present invention.

A graphical user interface may be used to assist a user in performing the steps discussed previously. FIG. 6 illustrates a GUI 600 according to one embodiment of present invention. FIG. 6 is given by way of example only. As can be seen in FIG. 6, The GUI 600 has several unique features. The "Back" button 610 allows the user to backup to fix errors (e.g. move backward from Step 404 to Step 402). The "ArchiveSave" button 620 allows the user to save his work at any given step and to later resume the method at that step. As noted previously, Steps 400-418 may be ordered differently than that shown in FIG. 4. The GUI 600 allows the user to practice the steps of the previously described method in a manner flexible to the user. The GUI 600 also allows the user to select a 3D ultrasound image 630 from among a plurality of 3D ultrasound images 640. Likewise, the GUI 600 allows the user to select fluoroscopy images 650 for analysis. The GUI 600 also allows the user to visualize the determined 3D seed positions with respect to the 3D ultrasound image.

Figure 7:
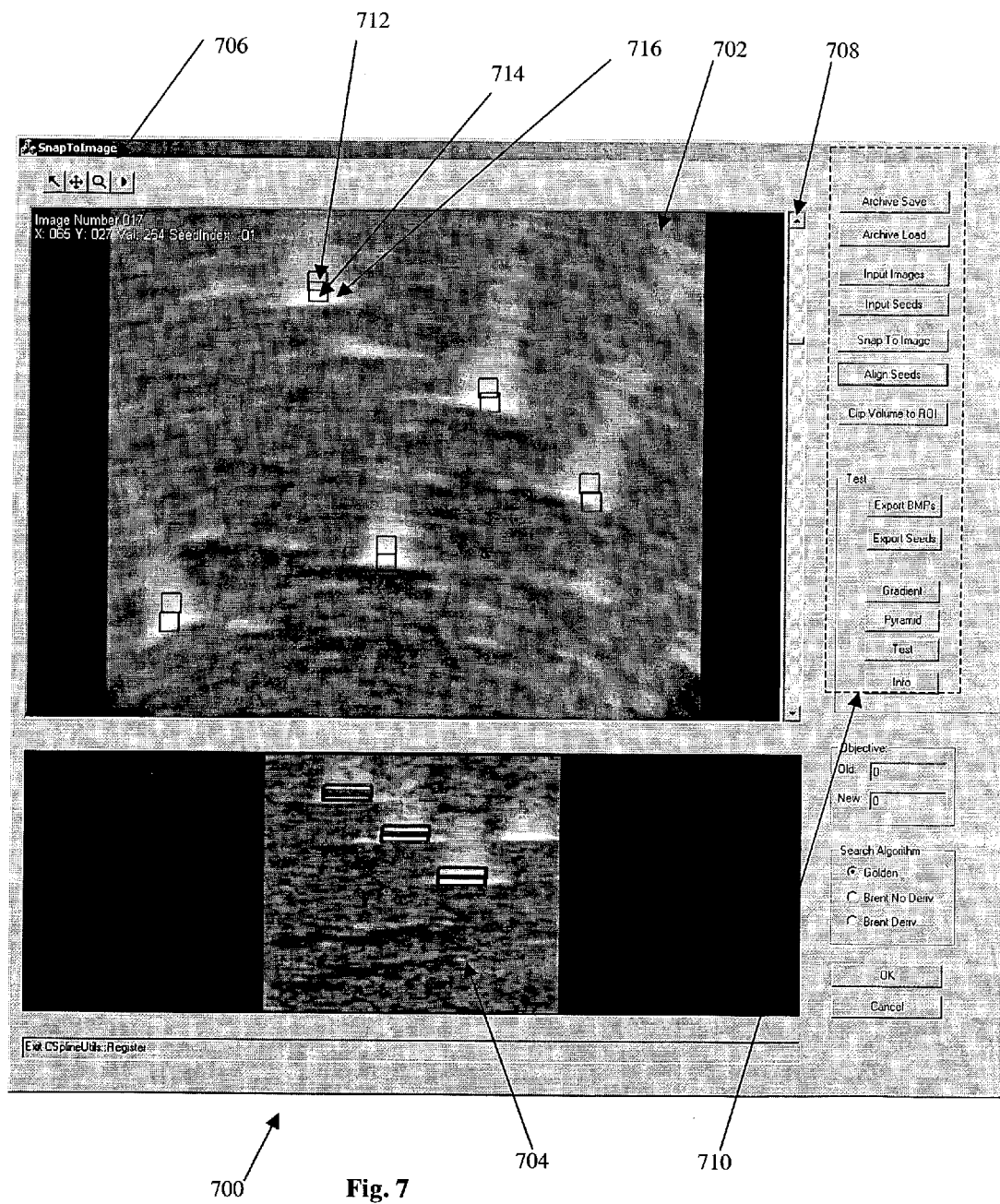
FIG. 7 is a screen shot display of a graphical user interface according to another embodiment of the present invention.

FIG. 7 shows a GUI 700 according to another embodiment of the present invention. The GUI 700 includes a first window 702 showing an ultrasound image in a X-Y plane, and a second window 704 showing an ultrasound image in a Z-Y plane. As such, the first and second windows 702 and 704 display transverse and longitudinal slices through the 3D ultrasound volume, respectively. The GUI 700 also includes control buttons 706 for manipulating or adjusting images in the first window 702 and the second window 704, scroll bar 708 for navigating through the image shown in the first window 702, and additional control buttons 710 for performing a number of functions associated with the method 200 described herein.

The GUI 700 also includes identifiers 712 and 714 that are shown together with the ultrasound images, thereby forming an improved 3D image of the region of the implanted seeds 40. The identifiers 712 having dotted lines represents the initial seed positions (i.e. the set $S_U$ calculated using the initial transformation T from step 506), and the identifiers 714 having solid lines indicate the final optimized seed positions (i.e. the set $S_U$ calculated using the final optimized transformation T from step 508). The identifiers 714 are at or in close proximity to the actual seed position, as identified by the bright pixels 716. Similar identifiers are also displayed in the second window 704, as shown in the illustrated embodiment. The identifiers 712 and 714 may be color-coded or may have shapes other than rectangles in alternative embodiments.

As discussed previously, the seed localization system 100 may include a user interface, such as the user interface 150, for guiding the user in accomplishing Steps 400-418 of the method 200. The user interface 150 is preferably implemented on the computer system 110 using the monitor 115, the keyboard 120, and the mouse 125 in the manner known to those skilled in the art. The user interface 150 forms an improved 3D image of the region of implanted seeds 40 by analyzing ultrasound and fluoroscopy data. The user interface 150 then allows the user to identify the location of each implanted seed 40 in the region by displaying the improved 3D image (i.e., through GUI 600 and/or 700).

Figure 8:
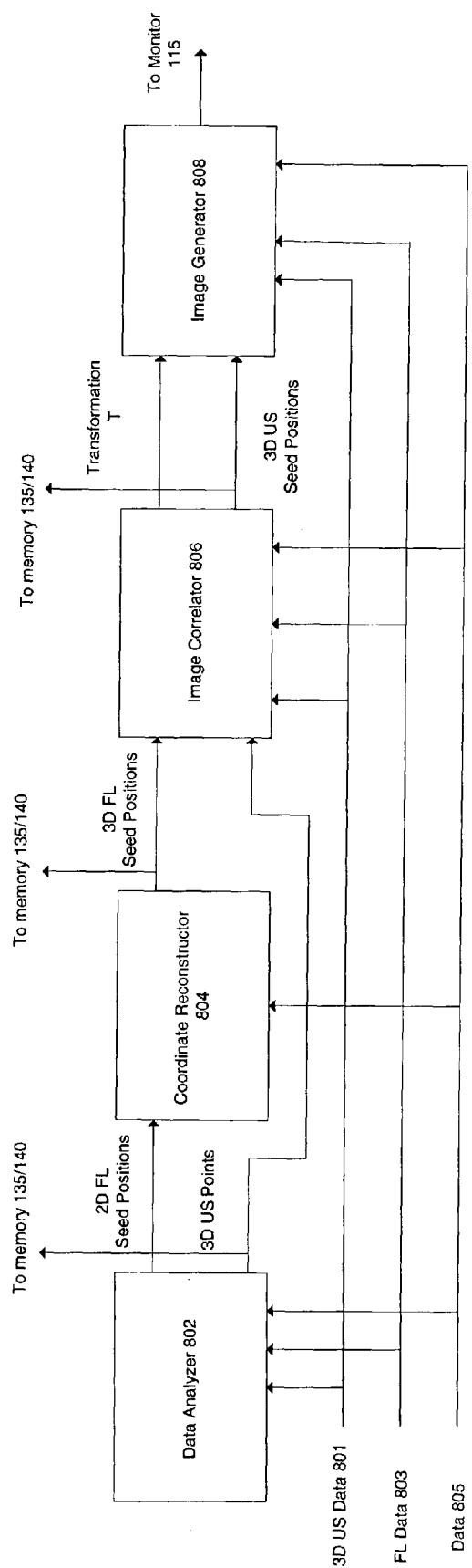
FIG. 8 is a block diagram of the structure of a user interface of an embodiment of the present invention.

FIG. 8 illustrates one embodiment of the user interface 150 in greater detail. Through the processor 130, the user interface 150 interacts with data input sources such as the keyboard 120, the mouse 125, the memory 135, and the hard disk 140. The user interface 150 also interacts with the medical image interface 170 as well as the network interface 160 via the processor 130.

From any of these data sources, the user interface 150 is provided with 3D ultrasound data 801 associated with the 3D ultrasound image volume obtained in Step 402, and fluoroscopy data 803 associated with the fluoroscopy images obtained in Step 404. The data analyzer 802 may also be provided with data 805 input from sources 120, 125, 135, 140, 160, or 170, which may be used to analyze the 3D ultrasound data 801 and/or the fluoroscopy data 803.

The data analyzer 802 analyzes the fluoroscopy data 803. In particular, the data analyzer 802 locates each seed 40 appearing in each fluoroscopy image comprised within the fluoroscopy data 803 according to Step 406. As previously noted, in one embodiment of the invention, the user may provide input 805 to locate each implanted seed 40 appearing in each fluoroscopy image. In an alternative embodiment, the data analyzer 802 may automatically locate each seed 40 using a variety of discrimination techniques known to those skilled in the art. In one embodiment of the invention, the data analyzer 802 stores the 2D fluoroscopy coordinates of each seed 40 in a memory. By way of example only, the memory in which the 2D fluoroscopy coordinates are stored may be memory associated with the personal computer of the system 100, such as memory areas 135 or 140.

The 2D positions of each seed 40 appearing on the fluoroscopy images are analyzed by a coordinate reconstructor 804, which associates the seeds 40 between or among the fluoroscopy images according to Step 408. The coordinate reconstructor 804 then reconstructs the 3D fluoroscopy coordinates of the seeds 40 according to Step 410. In one embodiment of the invention, the coordinate reconstructor 804 stores the coordinates for later recall and processing. By way of example only, the memory in which the 3D fluoroscopy coordinates are stored may be memory associated with the personal computer of the system 100, such as memory areas 135 or 140.

The data analyzer 802 may also analyze the 3D ultrasound data 801. For example, the data analyzer 802 may detect points in the 3D ultrasound image that are likely to be locations of seeds 40 according to Step 502. Alternatively, the user may provide input 805 to locate some of the seeds 40, as previously noted. The data analyzer 802 stores the 3D ultrasound coordinates of the detected or input points of the seeds 40 in a memory, such as memory areas 135 or 140.

A coordinate correlator 806 determines the transformation T that best matches the 3D fluoroscopy coordinates of the seeds 40 with the 3D ultrasound coordinates of the detected or input points according to Step 412. Based on the transformation T, the coordinate correlator 806 then maps each 3D fluoroscopy coordinate provided by the coordinate generator 804 to its corresponding 3D ultrasound location according to Step 414.

An image generator 808 then generates an image that displays a seed's position within the 3D ultrasound image according to Step 416 such that a user may visualize the image on the monitor 115. For example, the image generator 808 may cause the seed localization system 100 to display the GUI 600 or GUI 700 in the monitor 115.

Thus, a system and a method have been shown for determining the three-dimensional (3D) positions of implanted brachytherapy seeds with respect to an area of affected tissue. The system and method allow the practitioner to calculate a radiotherapy dose by examining images generated using ultrasound and fluoroscopy imaging but not requiring computed tomography imaging. The system may incorporate portable C-arm fluoroscopy systems as well. There is no requirement to use a fixed (pre-determined) fluoroscopy imaging geometry or to accurately calibrate the fluoroscopy images (e.g. each fluoroscopy image may have a different, unknown magnification). There is also no requirement for a fixed external, fiducial system, or an internal fiducial system (i.e., internal markers).

Further, because the present invention reconstructs the seed positions from fluoroscopic images rather than from other images, the invention may be practiced in a wider variety of settings than was possible in the prior art. For example, the invention may be practiced in an operating room. There is no need for a radiotherapy simulator couch or other specialized equipment.

Because the invention may be practiced intraoperatively, the invention does not require the patient to be carefully repositioned in another room having specialized medical imaging equipment. Further, the inventive system and method differs from the prior art in that seed positions are not determined based on planned, pre-implant seed coordinates but rather on the actual 3D seed positions at the time of implant in the most recently acquired ultrasound treatment volume/image. Thus, the 3D seed locations are identified much more accurately than in prior art systems and the user may validate the result. The dosimetry to the tissue under treatment may be determined intraoperatively, permitting dynamic adjustment of the treatment plan.

Although brachytherapy seeds used in the treatment of prostate have been discussed with reference to various embodiments, it should be understood that the scope of the invention should not be so limited. In an alternative embodiment, the seeds 40 may represent implanted objects other than brachytherapy seeds. In another alternative embodiment, the tissue to be treated may be tissue other than prostate 20. Furthermore, although the system and method have been described with reference to registering implant coordinate between a fluoroscopy and an ultrasound imaging systems, the system and method described previously may also be used to register implant position between other imaging systems.

Thus, although several preferred embodiments have been shown and described, it would be apparent to those skilled in the art that many changes and modifications may be made thereunto without the departing from the scope of the invention, which is defined by the following claims and their equivalents.

What is claimed:

1. A method for locating an implant in an ultrasound coordinate system, comprising:
   obtaining positions of a plurality of implants in a fluoroscopy coordinate system;
   estimating positions of said plurality of implants in an ultrasound coordinate system;
   using a processor to determining determine an initial transformation matrix based at least in part on said obtained positions and said estimated positions of said plurality of implants;
   using the processor to determine a position of one of said implants in said ultrasound coordinate system based at least in part on said initial transformation, wherein said position of said one of said implants is determined without requiring use of a plurality of markers that are different from the plurality of implants; and storing said determined position in a non-transitory medium or displaying said determined position on a screen.

2. The method of claim 1, wherein said plurality of implants comprises brachytherapy seeds.

3. The method of claim 1, wherein said plurality of implants comprises at least three implants or at least four implants.

4. The method of claim 1, further comprising refining said initial transformation matrix.

5. The method of claim 4, wherein said refining comprises determining a characteristic of a pixel at said determined position of said implant in an ultrasound image.

6. The method of claim 5, wherein said characteristic of said pixel comprises color or brightness.

7. The method of claim 5, wherein said refining further comprises determining a characteristic of a pixel associated with an actual position of said one of said implants in said ultrasound image.

8. The method of claim 7, wherein said refining further comprises assigning a value based at least in part on a comparison of said determined characteristic of said pixel at said determined position of said one of said treatment implants and said characteristic of said pixel associated with said actual position of said one of said implants in said ultrasound image.

9. The method of claim 8, wherein said refining further comprises modifying said transformation matrix based on said value.

10. The method of claim 9, wherein said modifying comprises minimizing said value.

11. The method of claim 4, wherein said position of said one of said implants in said ultrasound coordinate system is based at least in part on said refined initial transformation matrix.

12. The method of claim 11, further comprising displaying in an ultrasound image an identifier associated with said position that is determined based at least in part on said refined initial transformation matrix.

13. The method of claim 1, further comprising displaying in an ultrasound image an identifier associated with said determined position of said one of said implants.

14. The method of claim 1, further comprising determining a position of another one of said implants in said ultrasound coordinate system based at least in part on said initial transformation.

15. The method of claim 1, wherein said implants are more easily detectable using x-ray than ultrasound.

16. The method of claim 1, wherein the plurality of markers are for imaging, and the plurality of implants are for delivering radiation.

17. A computer program product, comprising:
   a non-transitory computer-readable medium having a sequence of instructions;
   wherein said sequence of instructions, when executed by a processor, causes the processor to execute a process, said process comprising obtaining positions of a plurality of implants in a fluoroscopy coordinate system, estimating positions of said plurality of implants in an ultrasound coordinate system, determining an initial transformation matrix based at least in part on said obtained positions and said estimated positions of said plurality of implants, and determining a position of one of said implants in said ultrasound coordinate system based at least in part on said initial transformation, wherein said position of said one of said implants is determined without requiring use of a plurality of markers that are different from the plurality of implants.

18. The product of claim 17, wherein said plurality of implants comprises brachytherapy seeds.

19. The product of claim 17, wherein said process further comprising refining said initial transformation matrix.

20. The product of claim 19, wherein said refining comprises determining a characteristic of a pixel at said determined position of said one of said implants in an ultrasound image.

21. The product of claim 20, wherein said refining further comprises determining a characteristic of a pixel associated with an actual position of said one of said implants in said ultrasound image.

22. The product of claim 21, wherein said refining further comprises assigning a value based at least in part on a comparison of said determined characteristic of said pixel at said determined position of said one of said implants and said characteristic of said pixel associated with said actual position of said one of said implants in said ultrasound image.

23. The product of claim 22, wherein said refining further comprises modifying said transformation matrix based on said value.

24. The product of claim 23, wherein said modifying comprises minimizing said value.

25. The product of claim 19, wherein said position of said one of said implants in said ultrasound coordinate system is based at least in part on said refined initial transformation matrix.

26. The product of claim 25, wherein said process further comprising displaying in an ultrasound image an identifier associated with said position that is determined based at least in part on said refined initial transformation matrix.

27. The product of claim 17, wherein said process further comprising displaying in an ultrasound image an identifier associated with said determined position of said one of said implants.

28. The computer program product of claim 17, wherein the plurality of markers are for imaging, and the plurality of implants are for delivering radiation.

29. A method for locating an implant in an ultrasound coordinate system, comprising:
  using a processor to determine an initial transformation based at least in part on positions of a plurality of implants in a fluoroscopy coordinate system and estimated positions of said plurality of implants in an ultrasound coordinate system;
  modifying said initial transformation based on an accuracy of said estimated positions of said plurality of implants;
  using the processor to determine a position of one of said implants in said ultrasound coordinate system based at least in part on said modified transformation, wherein said position of said one of said treatment implants is determined without requiring use of a plurality of imaging markers that are different from the plurality of implants; and
  storing said determined position in a non-transitory medium or displaying said determined position on a screen.

30. The method of claim 29, wherein said plurality of implants comprises brachytherapy seeds.

31. The method of claim 29, further comprising determining a position of said implant based on said initial transformation.

32. The method of claim 31, wherein said modifying comprises determining a characteristic of a pixel at said determined position of said one of said implants in an ultrasound image.

33. The method of claim 32, wherein said modifying further comprises determining a characteristic of a pixel associated with an actual position of said one of said implants in said ultrasound image.

34. The method of claim 33, wherein said modifying further comprises assigning a value based at least in part on a comparison of said determined characteristic of said pixel at said determined position of said one of said implants and said characteristic of said pixel associated with said actual position of said one of said implants in said ultrasound image.

35. The method of claim 29, wherein the one of said implants that is more easily detectable using x-ray than ultrasound.

36. A computer program product, comprising:
  a non-transitory computer-readable medium having a sequence of instructions;
  wherein said sequence of instructions, when executed by a processor, causes the processor to execute a process, said process comprising
    determining an initial transformation based at least in part on positions of a plurality of implants in a fluoroscopy coordinate system and estimated positions of said plurality of implants in an ultrasound coordinate system,
    modifying said initial transformation based on an accuracy of said estimated positions of said plurality of implants, and
    determining a position of one of said implants in said ultrasound coordinate system based at least in part on said modified transformation, wherein said position of said one of said implants is determined without requiring use of a plurality of markers that are different from the plurality of implants.

37. The product of claim 36, wherein said plurality of implants comprises brachytherapy seeds.

38. The product of claim 36, wherein said process further comprising determining a position of said one of said implants based on said initial transformation.

39. The product of claim 38, wherein said modifying comprises determining a characteristic of a pixel at said determined position of said one of said implants in an ultrasound image.

40. The product of claim 39, wherein said modifying further comprises determining a characteristic of a pixel associated with an actual position of said one of said implants in said ultrasound image.

41. The product of claim 40, wherein said modifying further comprises assigning a value based at least in part on a comparison of said determined characteristic of said pixel at said determined position of said one of said implants and said characteristic of said pixel associated with said actual position of said one of said implants in said ultrasound image.

42. The computer program product of claim 36, wherein the plurality of markers are for imaging, and the plurality of implants are for delivering radiation.

43. A method for locating an implant in an ultrasound coordinate system, comprising:
  providing a position of an implant in a fluoroscopy coordinate system;
  using a processor to transform said position of said implant in said fluoroscopy coordinate system to a coordinate for said implant in an ultrasound coordinate system; and storing said coordinate in a non-transitory medium or displaying said coordinate on a screen;
wherein said processor is used to transform said position of said implant in said fluoroscopy coordinate system without requiring use of a marker that is different from the implant.

44. The method of claim 43, wherein said implant comprises a brachytherapy seed.

45. The method of claim 43, wherein said processor is used to transform said position of said implant in said fluoroscopy coordinate system by determining an initial transformation.

46. The method of claim 45, wherein said processor is used to transform said position of said implant in said fluoroscopy coordinate system by also refining said initial transformation.

47. The method of claim 43, wherein said implant is more easily detectable using x-ray than ultrasound.

48. A system for determining a position of an implant in an ultrasound coordinate system, comprising:
a processor configured to determine an initial transformation based at least in part on positions of a plurality of implants in a fluoroscopy coordinate system and estimated positions of said plurality of treatment implants in an ultrasound coordinate system, and modify said initial transformation based on an accuracy of said estimated positions of said plurality of implants;
wherein said processor is further configured to determine a position of one of said implants in said ultrasound coordinate system based at least in part on said modified transformation without requiring use of a plurality of markers that are different from the plurality of treatment implants.

49. The system of claim 48, wherein said plurality of implants comprises brachytherapy seeds.

50. The system of claim 48, wherein said processor is configured to determine said accuracy of said estimated positions.

51. The system of claim 48, wherein said processor is configured to compare a characteristic of a pixel associated with an actual position of said one of said treatment implants in an ultrasound coordinate system with a characteristic of a pixel associated with a calculated position of said one of said implants in said ultrasound coordinate system, said calculated position determined based on said initial transformation, and wherein said accuracy is determined based on said comparison.

52. The system of claim 48, wherein said processor is configured to receive or determine an error value associated with said accuracy, and said processor is configured to modify said initial transformation based on said error value.

53. The system of claim 48, further comprising a monitor coupled to said processor.

54. The system of claim 53, wherein said processor is configured to display in said monitor an ultrasound image and an identifier associated with one of said estimated positions.

55. The system of claim 53, wherein said processor is configured to display in said monitor an ultrasound image and an identifier associated with said position of said one of said implants.

56. The system of claim 48, wherein the plurality of markers are for imaging, and the plurality of implants are for delivering radiation.

57. A system for locating an implant in an ultrasound coordinate system, comprising:
a processor configured for determining an initial transformation matrix based at least in part on positions of a plurality of branchytherapy seeds in a fluoroscopy coordinate system and estimated positions of said plurality of branchytherapy seeds in an ultrasound coordinate system, and determining a position of one of said plurality of branchytherapy seeds in said ultrasound coordinate system based at least in part on said initial transformation matrix;
wherein the processor is configured to determine the initial transformation matrix without requiring use of a plurality of markers that are different from the plurality of branchytherapy seeds.

58. The system of claim 57, wherein the plurality of markers are for imaging, and the plurality of branchytherapy seeds are for delivering radiation.

59. A method for locating a branchytherapy seed in an ultrasound coordinate system, comprising:
obtaining positions of a plurality of branchytherapy seeds in a fluoroscopy coordinate system, wherein the plurality of branchytherapy seeds includes at least four branchytherapy seeds;
estimating positions of the plurality of branchytherapy seeds in an ultrasound coordinate system;
using a processor to determine an initial transformation matrix based at least in part on the obtained positions and the estimated positions of the plurality of branchytherapy seeds;
refining the initial transformation matrix, wherein the act of refining comprises determining a color or a brightness of a pixel of one of the branchytherapy seeds in an image generated using ultrasound;
using the processor to determine a position of the one of the branchytherapy seeds in the ultrasound coordinate system based at least in part on the refined initial transformation, wherein the position of the one of said branchytherapy seeds is determined without requiring use of a plurality of markers that are different from the plurality of branchytherapy seeds; and
displaying in an ultrasound image an identifier associated with the determined position of the one of the branchytherapy seeds.

60. A system for determining a position of a branchytherapy seed in an ultrasound coordinate system, comprising:
a processor configured to:
obtain positions of a plurality of branchytherapy seeds in a fluoroscopy coordinate system, wherein the plurality of branchytherapy seeds includes at least four branchytherapy seeds, estimate positions of the plurality of branchytherapy seeds in an ultrasound coordinate system, determine an initial transformation matrix using an electronic processor based at least in part on the obtained positions and the estimated positions of the plurality of branchytherapy seeds, refine the initial transformation matrix, wherein the act of refining comprises determining a color or a brightness of a pixel of one of the branchytherapy seeds in an image generated using ultrasound;
determine a position of the one of the branchytherapy seeds in the ultrasound coordinate system based at least in part on the refined initial transformation, wherein the position of the one of said branchytherapy seeds is determined without requiring use of a plurality of markers that are different from the plurality of branchytherapy seeds, and transmit data to a display for displaying in an ultrasound image an identifier associated with the determined position of the one of the branchytherapy seeds.

* * * * *